(12) United States Patent
Jalisi et al.

(10) Patent No.: US 6,694,595 B1
(45) Date of Patent: Feb. 24, 2004

(54) METHOD OF MAKING A GUIDEWIRE CORE

(75) Inventors: Marc Mehrzad Jalisi, Temecula, CA (US); Mark Richardson, Escondido, CA (US); David M. Anderson, Temecula, CA (US); Wayne E. Cornish, Oceanside, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 178 days.

(21) Appl. No.: 09/635,713

(22) Filed: Aug. 9, 2000

Related U.S. Application Data

(62) Division of application No. 09/224,453, filed on Dec. 31, 1998, now Pat. No. 6,142,975.

(51) Int. Cl.$^7$ ................................ B23P 11/00
(52) U.S. Cl. ................ 29/505; 29/DIG. 11; 604/530
(58) Field of Search ........................ 604/524, 528, 604/530, 531, 264, 265, 270, 164.13, 526, 527, 170.1; 29/458, 508, 527.2, DIG. 11, 505, 514

(56) References Cited

U.S. PATENT DOCUMENTS

| | | | |
|---|---|---|---|
| 3,068,563 A | * 12/1962 | Reverman | 29/508 |
| 4,538,622 A | 9/1985 | Samson et al. | 128/772 |
| 4,748,986 A | 6/1988 | Morrison et al. | 128/772 |
| 4,917,104 A | 4/1990 | Rebell | 128/772 |
| 4,925,445 A | 5/1990 | Sakamoto et al. | 604/95 |
| 5,057,092 A | * 10/1991 | Webster, Jr. | 604/282 |
| 5,069,217 A | 12/1991 | Fleischhacker, Jr. | 128/657 |
| 5,069,226 A | 12/1991 | Yamauchi et al. | 128/772 |
| 5,135,503 A | 8/1992 | Abrams | 604/164 |
| 5,171,383 A | 12/1992 | Sagaye et al. | 148/564 |
| 5,213,111 A | 5/1993 | Cook et al. | 128/772 |

(List continued on next page.)

FOREIGN PATENT DOCUMENTS

| | | | | |
|---|---|---|---|---|
| EP | 382974 A1 | * | 8/1990 | A61M/25/01 |
| JP | 405200432 | * | 8/1993 | 29/508 |

Primary Examiner—David P. Bryant
Assistant Examiner—Jermie E. Cozart
(74) Attorney, Agent, or Firm—Fulwider Patton Lee & Utecht, LLP

(57) ABSTRACT

An intracorporeal device, preferably a guidewire, and method of making same that has an elongate inner core element with an outer layer of material disposed about the core element. The layer of material can be applied as a braid, strand or smooth layer of material, and is preferably a metal. If the layer of material is applied as a braid or strand, it may be subsequently cold drawn so as to create a smooth layer from the braid or strand. The inner core element, may be homogeneous, or may consist of drawn filled tubing with at least two layers of material, preferably biocompatible metals. In this way, the multiple layer distal section of the elongate core can be shaped or ground so as to achieve the desired mechanical properties and provide surfaces for attachment of components that are readily bonded or soldered to.

6 Claims, 2 Drawing Sheets

U.S. PATENT DOCUMENTS

| | | | | |
|---|---|---|---|---|
| 5,230,348 A | | 7/1993 | Ishibe et al. | 128/772 |
| 5,238,004 A | | 8/1993 | Sahatjian et al. | 128/772 |
| 5,253,653 A | | 10/1993 | Daigle et al. | 128/772 |
| 5,341,818 A | | 8/1994 | Abrams et al. | 128/772 |
| 5,345,945 A | | 9/1994 | Hodgson et al. | 128/772 |
| 5,506,059 A | | 4/1996 | Robbins et al. | 428/457 |
| 5,520,194 A | | 5/1996 | Miyata et al. | 128/772 |
| 5,538,513 A | * | 7/1996 | Okajima | 604/282 |
| 5,569,220 A | * | 10/1996 | Webster, Jr. | 604/282 |
| 5,588,443 A | | 12/1996 | Davidson | 128/772 |
| 5,591,142 A | * | 1/1997 | Van Erp | 604/282 |
| 5,607,463 A | | 3/1997 | Schwartz et al. | 623/1 |
| 5,628,787 A | | 5/1997 | Mayer | 623/1 |
| 5,630,840 A | | 5/1997 | Mayer | 623/1 |
| 5,636,641 A | | 6/1997 | Fariabi | 128/772 |
| 5,637,089 A | | 6/1997 | Abrams et al. | 604/95 |
| 5,647,858 A | | 7/1997 | Davidson | 604/264 |
| 5,664,580 A | | 9/1997 | Erickson et al. | 128/772 |
| 5,674,208 A | * | 10/1997 | Berg et al. | 604/282 |
| 5,695,111 A | | 12/1997 | Nanis et al. | 228/206 |
| 5,720,300 A | | 2/1998 | Fagan et al. | 128/772 |
| 5,725,570 A | | 3/1998 | Heath | 623/1 |
| 5,725,572 A | | 3/1998 | Lam et al. | 623/1 |
| 5,733,326 A | | 3/1998 | Tomonto et al. | 623/1 |
| 5,824,056 A | | 10/1998 | Rosenberg | 623/1 |
| 5,824,077 A | | 10/1998 | Mayer | 623/11 |
| 5,827,201 A | * | 10/1998 | Samson et al. | 604/281 |
| 5,843,166 A | | 12/1998 | Lentz et al. | 623/1 |
| 5,891,191 A | | 4/1999 | Stinson | 623/1 |
| 5,951,495 A | * | 9/1999 | Berg et al. | 600/585 |
| 6,026,555 A | * | 2/2000 | Sager | 29/458 |
| 6,106,510 A | * | 8/2000 | Lunn et al. | 604/524 |
| 6,197,014 B1 | * | 3/2001 | Samson et al. | 604/524 |
| 6,290,692 B1 | * | 9/2001 | Klima et al. | 604/524 |

* cited by examiner

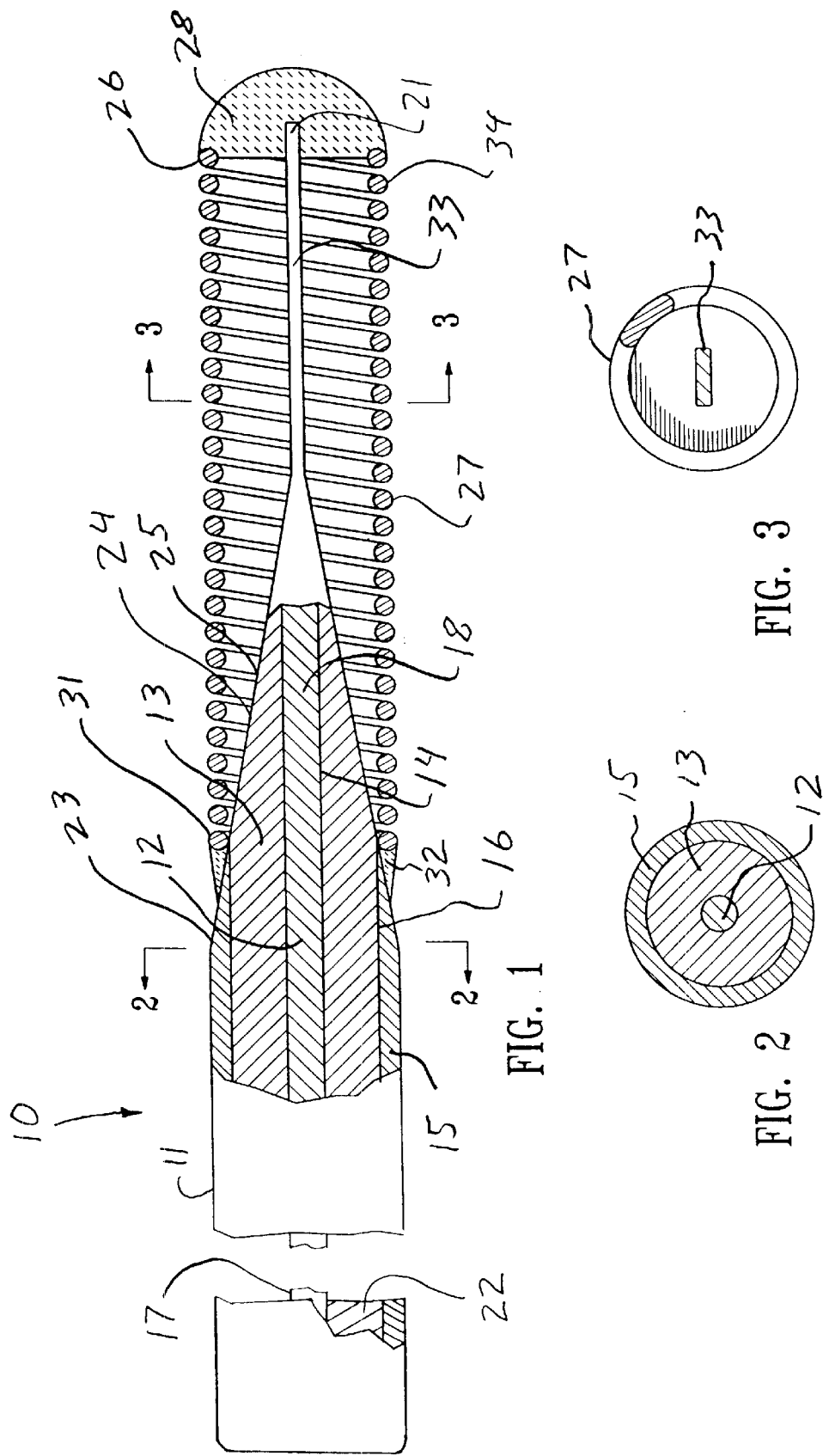

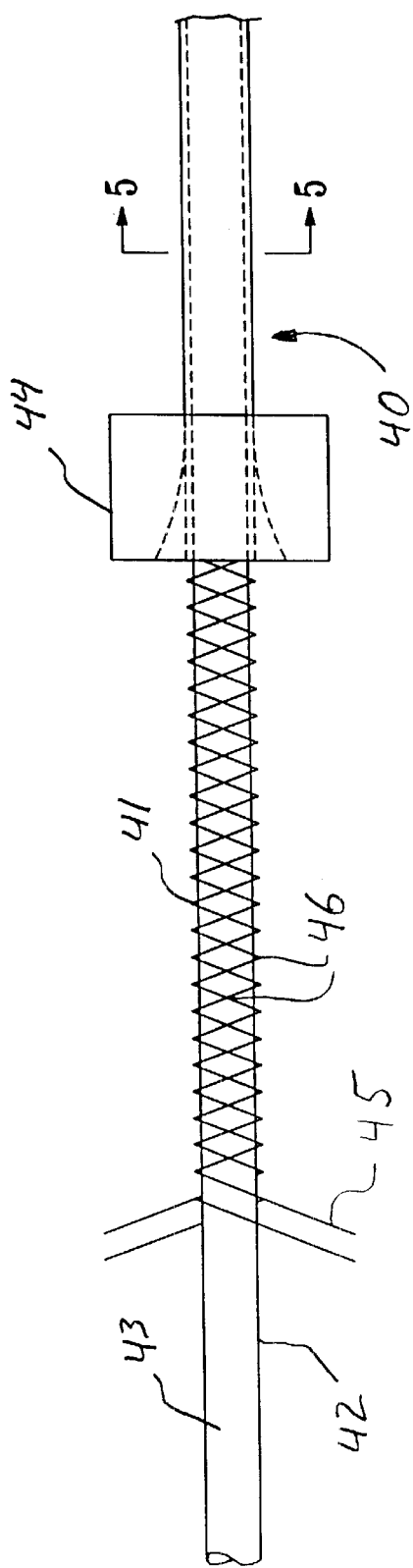
FIG. 4
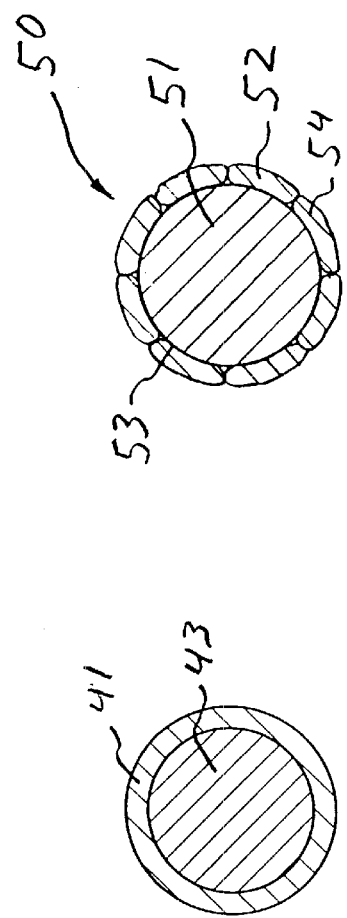
FIG. 5
FIG. 6

METHOD OF MAKING A GUIDEWIRE CORE

This is a divisional application of application Ser. No. 09/224,453 filed on Dec. 31, 1998, now U.S. Pat. No. 6,142,975, all of which are incorporated by reference.

BACKGROUND OF THE INVENTION

This invention relates to the field of guidewires for advancing intraluminal devices such as stent delivery catheters, balloon dilatation catheters, atherectomy catheters and the like within body lumens.

Conventional guidewires for angioplasty and other vascular procedures usually comprise an elongated core member with one or more tapered sections near the distal end thereof and a flexible body such as a helical coil disposed about the distal portion of the core member. A shapable member, which may be the distal extremity of the core member or a separate shaping ribbon which is secured to the distal extremity of the core member extends through the flexible body and is secured to a rounded plug at the distal end of the flexible body.

In a typical coronary procedure, a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the procedure is performed.

A requirement for guidewires is that they have sufficient column strength to be pushed through a patient's vascular system or other body lumen without kinking. However, they must also be flexible enough to avoid damaging the blood vessel or other body lumen through which they are advanced. Efforts have been made to improve both the strength and flexibility of guidewires to make them more suitable for their intended uses, but these two properties are for the most part diametrically opposed to one another in that an increase in one usually involves a decrease in the other.

Further details of guidewires, and devices associated therewith for various interventional procedures can be found in U.S. Pat. No. 4,748,986 (Morrison et al.); U.S. Pat. No. 4,538,622 (Samson et al.); U.S. Pat. No. 5,135,503 (Abrams); U.S. Patent 5,341,818 (Abrams et al.); and U.S. Pat. No. 6,345,945 (Hodgson et al.) which are hereby incorporated herein in their entirety by reference thereto.

Pseudoelastic alloys can be used to achieve both flexibility and strength. When stress is applied to NiTi alloy exhibiting pseudoelastic characteristics at a temperature at or above which the transformation of martensite phase to the austenite phase is complete, the specimen deforms elastically until it reaches a particular stress level where the alloy then undergoes a stress-induced phase transformation from the austenite phase to the martensite phase, As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress are necessary to cause further deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as pseudoelasticity. These properties to a large degree allow a guidewire core of a psuedoelastic material to have both flexibility and strength. However, psuedoelastic alloy components are typically difficult to join or secure to other components. This is due primarily to a tenacious oxide layer that develops on the surface of some such alloys, particularly those containing titanium.

Prior methods of pre-treatment for securing subassemblies to a distal core made of pseudoelastic alloys such as NiTi include molten or fusion salt etching and then pretinning the core to facilitate forming a strong bond, as seen in U.S. Pat. No. 6,695,111 to Nanis et al. which is hereby incorporated in its entirety by reference. While this method represents a significant advance, what has been needed is a method for manufacturing a guidewire with a superelastic or psuedoelastic component which will allow the component to accept a weld, solder or adhesive joint with ease of manufacture and low cost. It is also desirable to have a manufacturing process in which the mechanical properties of psuedoelastic and high strength alloys can be combined.

SUMMARY OF THE INVENTION

The present invention is directed to an intracorporeal device, preferably a guidewire, and method for making the device. The guidewire has an elongate core member with a proximal section and a distal section. The elongate core has an inner core element of a desired metal and an outer layer of material disposed about the inner core element. The outer layer of material is typically applied to the inner core element as a braid which is then cold drawn through a die which conforms and secures the outer layer to the inner core element. The outer layer of material may be cold drawn to a smooth continuous layer, or may be cold drawn to a lesser extent where the outer layer maintains a braided flattened configuration.

In an alternative embodiment of the invention, an elongate core member has a second outer layer of material applied to an inner core element and a first outer layer of material which may be drawn filled tubing. The drawn filled metallic tubing preferably consists of an inner core element of stainless steel and a first outer layer of psuedoelastic alloy, normally consisting of NiTi alloy disposed about the inner core element. The second outer layer of braided stainless steel is applied and cold drawn through a die so as to create an elongate core member having a layer of NiTi alloy sandwiched between an inner core element and an outer layer of stainless steel. When the distal section of this elongate core member is tapered to a distally smaller cross section, the various layers of the elongate core member are exposed.

Typically, a flexible body is disposed over and secured to at least a portion of the distal section of the elongate core member. The flexible body can be a helical spring but can also be a polymer jacket of material that can be thin or sufficiently thick to provide a diameter similar to that of the proximal section.

The distal end of the helical coil, or other flexible body, is preferably secured to a distal end of the elongated core member, by soldering, brazing, welding, bonded polymeric materials or other suitable means.

The inner core element, which is preferably stainless steel or other suitable high strength bondable or solderable material, is exposed at the distal end of the elongate core member as a result of the tapering of the distal section. Exposure of the inner core element allows the distal end of the flexible body to ha bonded or soldered to the distal end of the bondable or solderable material of the inner core element. A proximal end of the flexible body is preferably bonded or soldered to a distal section of the second outer layer of material. Preferably, the second outer layer of material is comprised of stainless steel or some other suitable bondable or solderable material. In this way, the flexible body will have its distal and proximal ends secured to bondable or solderable materials. If the first outer layer of material is made of a pseudoelastic alloy, a desired amount of the distal section can exhibit mechanical properties of the pseudoelastic alloy which comprises the majority of the distal section material. This results in high strength bonding or soldering between the guidewire components, smooth flexibility transitions in the elongate core member and the desired pseudoelastic mechanical characteristics in the distal section of the elongate core member. In addition to solderablity and bondability, the outer layers of material may be selected for desired mechanical strength properties. For example, a second outer layer of material may be made from a precipitation hardenable alloy such as MP35N in order to give the proximal section of the elongate core member a desired amount of strength.

BRIEF DESCRIPTION OF THE DRAWINGS

FIG. 1 depicts a longitudinal cross sectional view of a guidewire having features of the invention.

FIG. 2 is a transverse cross sectional view of the guidewire of FIG. 1 taken at lines 2—2 in FIG. 1.

FIG. 3 is a transverse cross sectional view of the guidewire of FIG. 1 taken at lines 3—3 in FIG. 1.

FIG. 4 is a schematic view of an outer layer of material being braided onto an inner core element and cold drawn.

FIG. 5 is a transverse cross sectional view of the outer layer of material and inner core element of FIG. 4 taken at lines 5—5 in FIG. 4.

FIG. 6 is a transverse cross sectional view of a stranded outer layer of material over an inner core element.

DETAILED DESCRIPTION OF THE INVENTION

FIG. 1 is a longitudinal cross sectional view of a guidewire 10 having features of the invention. An elongate core member 11 has an inner core element 12, a first outer layer of material 13 disposed on an outer surface 14 of the inner core element, and a second outer layer of material 15 disposed on an outer surface 16 of the first outer layer of material. The first outer layer of material 13 and second outer layer of material 15 are shown as smooth continuous layers. The inner core element 12 has a proximal section 17, a distal section 18 and a distal end 21. The second outer layer 15 has a proximal section 22 and a distal section 23. A distal section 24 of the elongate core member 11 has a distally tapered segment 25 which can be adjusted in length, taper angle and cross sectional shape to achieve the desired flexibility and performance characteristics for the guidewire 10. The distally tapered segment 25 also serves to expose the distal end 21 of the inner core element 12 to which a distal end 26 of a flexible body 27 is secured. The distal end 26 of the flexible body 27 is secured to the distal end 21 of the inner core element 12 by a first body of solder 28. A proximal end 31 of the flexible body 27 is secured to the distal section 23 of the second outer layer of material 15 with a second body of solder 32. Although a single distally tapered segment 25 is shown, the distal section 24 of the elongate core member 11 may have two or more such tapered segments which may or may not be separated by segments of substantially constant diameter.

A flexible body 27, such as a helical coil, polymer jacket, or the like, surrounds and covers at least a portion of the distal section 24 of the elongate core member 11. Polymers suitable for forming a flexible body 27 can include polyimide, polyethylene, polyurethane, TFE, PTFE, ePTFE and other similar materials. A flexible body 27 in the form of a helical coil may be formed of a suitable radiopaque material such as tantalum, gold, iridium, platinum or alloys thereof or formed of other material such as stainless steel and coated with a radiopaque material such as gold. The wire from which the coil is made generally has a transverse diameter of about 0.001 to about 0.004 inch, preferably about 0.002 to about 0.003 inch (0.05 mm). Multiple turns of a distal portion of coil 27 may be expanded to provide additional flexibility. The helical coil 27 may have transverse dimensions about the same as a proximal core section 35. The coil 27 may have a length of about 2 to about 40 cm or more, but typically will have a length of about 2 to about 10 cm in length.

The inner core element 12 and second outer layer of material 16 are made of stainless steel but can also be made of any other suitable solderable or bondable high strength materials. The first outer layer of material 13 disposed between the inner core element 12 and the second outer layer of material 15 is a pseudoelastic alloy, more specifically, NiTi alloy, which is chosen for its mechanical properties and performance. The first outer layer of material may also be made of any suitable metal or alloy having desired properties. The inner core element 12, first outer layer of material 13, and second outer layer of material 15 may be formed of stainless steel, NiTi alloys, MP35N, L605 or combinations thereof such as described in U.S. Pat. No. 5,341,818 (Abrams at al) which is incorporated herein in its entirety. Other materials such as the high strength alloys as described in U.S. Pat. No. 5,636,641 (Fariabi), entitled HIGH STRENGTH MEMBER FOR INTRACORPOREAL USE, which is incorporated herein by reference, may also be used.

As is known in the art, many materials used for guidewire construction have desirable mechanical properties, but are difficult to assemble to other guidewire components using conventional technology such as soldering or use of polymer adhesives due to inherent surface properties such as tenacious oxide layers. The construction shown in FIG. 1 allows the use of materials which have poor bondability or solderability, such as NiTi alloy in a guidewire core without concern for the bondability or solderability of the material.

FIG. 2 shows a transverse cross sectional view of the guidewire 10 of FIG. 1 taken at lines 2—2 in FIG. 1. The inner core element 12 is surrounded by a substantially coaxial or concentric first outer layer of material 13. The first outer layer of material 13 is surrounded by a second outer layer of material 15. The inner core element has a nominal transverse dimension of up to 0.02 inches, preferably about 0.005 to about 0.01 inches more preferably about 0.006 to about 0.008 inches. The first outer layer of material 13 and second outer layer of material 15 have a nominal wall thickness of up to about 0.015 inches, preferably about 0.0005 to about 0.01 inches, and more preferably about 0.001 to about 0.003 inches. Although the inner core element 12 is shown as solid, the inner core element may also be hollow with a lumen extending longitudinally therethrough. A lumen extending longitudinally through the inner core element 12 could be used for delivery of diagnostic or therapeutic agents, such as radioactive therapy agents or growth factors or the like. The lumen may also be used for advancement of elongated medical devices into a patient's vasculature.

FIG. 3 shows a transverse cross sectional view of the guidewire 10 of FIG. 1 taken at lines 3—3 in FIG. 1. The flexible body 27 is disposed partially about a distal segment 33 of the elongate core member 11. Referring back to FIG. 1, distal segment 33 is configured to provide a highly flexible segment at a distal end 34 of the guidewire 10 in order to facilitate advancement through a patient's vasculature without causing injury thereto. The distal segment 33 is shown as a flattened portion of the exposed inner core element 12 which facilitates shapeability of the distal segment, however, the flexible segment can have a round cross section, or any other suitable configuration.

FIG. 4 illustrates a portion of a method having features of the invention used to produce an elongate core member 40. An outer layer of material 41 is being braided onto an outer surface 42 of an inner core element 43. The inner core element 43 and outer layer of braided material 41 are drawn through a die 44 so as to compress the outer layer of braided material onto the outer surface 42 of the inner core element and produce a smooth coaxial layer of material thereon. The outer layer 41 may be cold drawn or co-drawn down to a smooth continuous layer, or may be partially cold drawn or co-drawn to a lesser extent where the outer layer retains a braided or stranded character that has been flattened against the outer surface 42 of the inner core member 43. It is desirable for the cold drawing or co-drawing process to create a bond between the inner core member 43 and the outer layer of material 41. The bond between the inner core member 43 and the outer layer of material 41. The bond between the inner core member 43 and the outer layer of material 41 can be partially or wholly mechanical. As used herein, the term braid or braided is intended to refer to the process or object resulting from the process of interweaving filaments 45 of material such that the individual filaments overlap each other at regular intervals or pick points 46. Such a braid can be produced in a cylindrical configuration by itself, or it can be formed over a mandrel such as the inner core element 43. A braid can be defined by the number of filaments 45, the transverse dimension of the filaments, the transverse dimension of the mandrel over which the braid is formed and the picks 46 per unit length as the braid is laid down. The term strand or stranded is intended to refer to the process or object resulting from the process of laying filaments of material in a single layer without overlap of the filaments. The filaments 45 of an outer layer of material 41 may all be of the same material or may be from a variety of different materials. For example, filaments 45 may all be stainless steel, or some may be stainless steel and others MP35N or NiTi alloy. Filaments of radiopaque materials such as gold, platinum, tantalum and the like may also be used.

FIG. 5 shows a transverse cross sectional view of the inner core element 43 and outer layer of material 41 after passing through the die 44. The inner core element 43 is shown as solid and non-layered, however, the inner core element may have multiple layers prior to the application of the outer layer of braided material 41. The multiple layering of the inner core element 43 may be achieved by the braiding and drawing through a die as discussed above, or the layers may be achieved by conventional drawn filled tubing techniques which are known in the art. In addition, the method depicted in FIG. 5 which shows an outer layer of material 41 applied as braid may also be achieved by applying the layer of material as a strand or other suitable configuration. An elongate core member 40 having four, five, six or more layers can be achieved by using the above described methods.

FIG. 6 shows a transverse cross section of an elongate core member 50 having an inner core element 51 and an outer layer of material 52. The outer layer of material 52 has been applied as a strand and partially cold drawn or co-drawn and retains a stranded character. The outer layer of material 52 has been flattened against an outer surface 53 of the inner core element 51 and is at least partially mechanically secured thereto. Individual filaments 64 can be seen in the outer layer of material 52.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A method of making an elongated guidewire core, comprising:
    a) applying an outer layer of material as a braid on at least a portion of an inner core element;
    b) cold drawing the braid and inner core element through a die to merge braid portions across gaps between the braid portions to form a smooth continuous layer; and
    c) distally tapering a section of the inner core element and braid to a desired tapered profile to form a guidewire core.

2. The method of claim 1 wherein the inner core element is comprised of a pseudoelastic alloy.

3. The method of claim 1 wherein the inner core element is comprised of NiTi.

4. The method of claim 1 wherein the outer layer of material is stainless steel.

5. The method of claim 1 wherein the step of applying an outer layer of material as a braid comprises completely joining the outer layer to the inner core element.

6. The method of claim 1 further comprising applying a second outer layer of material on at least a portion of the braid.

* * * * *

UNITED STATES PATENT AND TRADEMARK OFFICE
CERTIFICATE OF CORRECTION

PATENT NO. : 6,694,595 B1
DATED : February 24, 2004
INVENTOR(S) : Marc M. Jalisi et al.

It is certified that error appears in the above-identified patent and that said Letters Patent is hereby corrected as shown below:

Column 1,
Line 56, delete "6,345,945" and insert -- 5,345,945 --.

Column 2,
Line 32, delete "6,695,111" and insert -- 5,695,111 --.

Column 3,
Line 20, "delete "ha" and insert -- be --.

Column 4,
Line 42, delete "material 16" and insert -- material 15 --.

Signed and Sealed this

Seventeenth Day of August, 2004

JON W. DUDAS
*Acting Director of the United States Patent and Trademark Office*